(12) United States Patent
Lange et al.

(10) Patent No.: US 12,354,735 B2
(45) Date of Patent: Jul. 8, 2025

(54) SYSTEMS AND METHODS FOR CLASS OF TRADE RECOMMENDATIONS FOR A HEALTHCARE SITE

(71) Applicant: MCKESSON CORPORATION, Irving, TX (US)

(72) Inventors: Matthew Lange, Mequon, WI (US); Farzia Kaufman, Spring, TX (US); Alexander Labinov, Providence, RI (US); John Albaugh, Spring, TX (US); Jeffrey Bennish, Denver, CO (US); Adam Perry, Golden, CO (US); Ali Rastegarzadeh, Houston, TX (US)

(73) Assignee: MCKESSON CORPORATION, Irving, TX (US)

( * ) Notice: Subject to any disclaimer, the term of this patent is extended or adjusted under 35 U.S.C. 154(b) by 447 days.

(21) Appl. No.: 17/849,496

(22) Filed: Jun. 24, 2022

(65) Prior Publication Data
US 2023/0420117 A1 Dec. 28, 2023

(51) Int. Cl.
*G16H 40/20* (2018.01)
*G06Q 10/0639* (2023.01)

(52) U.S. Cl.
CPC ....... *G16H 40/20* (2018.01); *G06Q 10/06393* (2013.01)

(58) Field of Classification Search
CPC .......... G16H 40/20; G06Q 10/06393
See application file for complete search history.

(56) References Cited

U.S. PATENT DOCUMENTS

| | | | |
|---|---|---|---|
| 2006/0178905 A1* | 8/2006 | Ayers .................. | G06Q 10/10 705/26.44 |
| 2014/0358578 A1* | 12/2014 | Ptachcinski ........... | G06Q 10/10 705/2 |

OTHER PUBLICATIONS

Nathan Hagen et al., "Moving a 340B covered entity's pharmacy enterprise to an LLC may prove beneficial, but it requires a feasibility study," https://www.hfma.org/cost-effectiveness-of-health/financial-sustainability/moving-a-340b-covered-entity-s-pharmacy-enterprise-to-an-llc-may/ (Year: 2021).*
Brent Dykes, "Reporting APIs: How To Make Them Better, Stronger, Faster" https://www.forbes.com/sites/brentdykes/2020/03/25/reporting-apis-how-to-make-them-better-stronger-faster/ (Year: 2020).*

(Continued)

*Primary Examiner* — Joshua B Blanchette
(74) *Attorney, Agent, or Firm* — Ballard Spahr LLP

(57) ABSTRACT

Technologies are provided for class of trade recommendations for healthcare sites. In some embodiments, a computing system can access data indicative of operating conditions of a healthcare site over a historical time period, and can access second data indicative of fee schedules corresponding to respective classes of trade. The computing system can determine, based on the data and the second data, a performance metric for the healthcare site according to a first class of trade (COT) of the respective classes of trade, and can determine, based on the first data and the second data, the performance metric for the healthcare site according to a second COT of the respective classes of trade. The computing system can generate, based on the performance metric and the second performance metric, a recommendation to configure the healthcare site according to one of the first COT or the second COT, and can supply the recommendation.

20 Claims, 8 Drawing Sheets

(56) References Cited

OTHER PUBLICATIONS

A. Creswell, T. White, V. Dumoulin, K. Arulkumaran, B. Sengupta and A. A. Bharath, "Generative Adversarial Networks: An Overview," in IEEE Signal Processing Magazine, vol. 35, No. 1, pp. 53-65, Jan. 2018, doi: 10.1109/MSP.2017.2765202 (Year: 2018).*

* cited by examiner

FIG. 3C

SYSTEMS AND METHODS FOR CLASS OF TRADE RECOMMENDATIONS FOR A HEALTHCARE SITE

SUMMARY

It is to be understood that both the following general description and the following detailed description are illustrative and explanatory only and are not restrictive.

In an embodiment, the disclosure provides a computing system. The computing system includes at least one processor; and at least one memory device having processor-executable instructions stored thereon that, in response to execution by the at least one processor, cause the computing system to: access first data indicative of operating conditions of a healthcare site over a historical time period; access second data indicative of fee schedules corresponding to respective classes of trade; determine, based on the first data and the second data, a performance metric for the healthcare site according to a first class of trade (COT) of the respective classes of trade; determine, based on the first data and the second data, the performance metric for the healthcare site according to a second COT of the respective classes of trade; generate, based on the performance metric and the second performance metric, a recommendation to configure the healthcare site according to one of the first COT or the second COT; and supply the recommendation.

In another embodiment, the disclosure provides a computer-implemented method. The computer-implemented method includes accessing first data indicative of operating conditions of a healthcare site over a historical time period; and accessing second data indicative of fee schedules corresponding to respective classes of trade. The computer-implemented method also includes determining, based on the first data and the second data, a performance metric for the healthcare site according to a first class of trade (COT) of the respective classes of trade; and determining, based on the first data and the second data, a second performance metric for the healthcare site according to a second COT of the respective classes of trade. The computer-implemented method further includes generating, based on the performance metric and the second performance metric, a recommendation to configure the healthcare site according to one of the first COT or the second COT. The computer-implemented method still further includes and supplying the recommendation.

In yet another embodiment, the disclosure provides at least one computer-readable non-transitory storage medium having processor-executable instructions stored thereon that, in response to execution, cause a computing system to: access first data indicative of operating conditions of a healthcare site over a historical time period; access second data indicative of fee schedules corresponding to respective classes of trade; determine, based on the first data and the second data, a performance metric for the healthcare site according to a first class of trade (COT) of the respective classes of trade; determine, based on the first data and the second data, the performance metric for the healthcare site according to a second COT of the respective classes of trade; generate, based on the performance metric and the second performance metric, a recommendation to configure the healthcare site according to one of the first COT or the second COT; and supply the recommendation.

Additional elements or advantages of this disclosure will be set forth in part in the description which follows, and in part will be apparent from the description, or may be learned by practice of the subject disclosure. The advantages of the subject disclosure can be attained by means of the elements and combinations particularly pointed out in the appended claims.

This summary is not intended to identify critical or essential features of the disclosure, but merely to summarize certain features and variations thereof. Other details and features will be described in the sections that follow. Further, both the foregoing general description and the following detailed description are illustrative and explanatory only and are not restrictive of the embodiments of this disclosure.

BRIEF DESCRIPTION OF THE DRAWINGS

The annexed drawings are an integral part of the disclosure and are incorporated into the subject specification. The drawings illustrate example embodiments of the disclosure and, in conjunction with the description and claims, serve to explain at least in part various principles, elements, or aspects of the disclosure. Embodiments of the disclosure are described more fully below with reference to the annexed drawings. However, various elements of the disclosure can be implemented in many different forms and should not be construed as limited to the implementations set forth herein. Like numbers refer to like elements throughout.

FIG. 3C illustrates another example of a user interface, in accordance with one or more embodiments of this disclosure.

DETAILED DESCRIPTION

The disclosure recognizes and addresses, among other technical challenges, the issue of identification of a class of trade that is appropriate for operating state of a healthcare site. Class of trade (COT) is an industry designation that characterizes various aspects of the operation of a healthcare site, and also can dictate how the healthcare site interacts with other entities in a health provider ecosystem. For healthcare sites, classes of trade can include hospital outpatient department (HOPD) clinic (referred to as "Hospital COT") and physician-based clinic (referred to as "Clinic COT"). Embodiments of this disclosure provide computing systems, computing devices, computer-implemented methods, and computer program products that, individually or in combination, can provide a recommendation for COT for a healthcare site. The healthcare site can be, for example, an oncology site where patients having cancerous bodily tissues can be treated. The oncology site can be a practice operating according to a particular class of trade. That practice can be, in some cases, a non-340B practice. Other types of healthcare sites also are contemplated, such as a rheumatology site, a neurology site, a long-term care site, an ambulatory infusion center, a home-based infusion site, or a pharmacy.

To generate a recommendation, various types of data are accessed and then normalized in order to generate data that can be directly and accurately compared across classes of trade. The data can include first historical data defining values of operational attributes corresponding to a drug acquisition category, and second historical data defining values of operational attributes corresponding to a procedure category. The data also can include first data indicative of fee schedules for respective classes of trade. After that data has been normalized, a performance metric for a healthcare site can be evaluated under different classes of trade, e.g., Hospital COT and Clinic COT. A recommendation for a particular COT for the healthcare site can be generated based on values of such performance metric under the different classes of trade.

Figure 1:
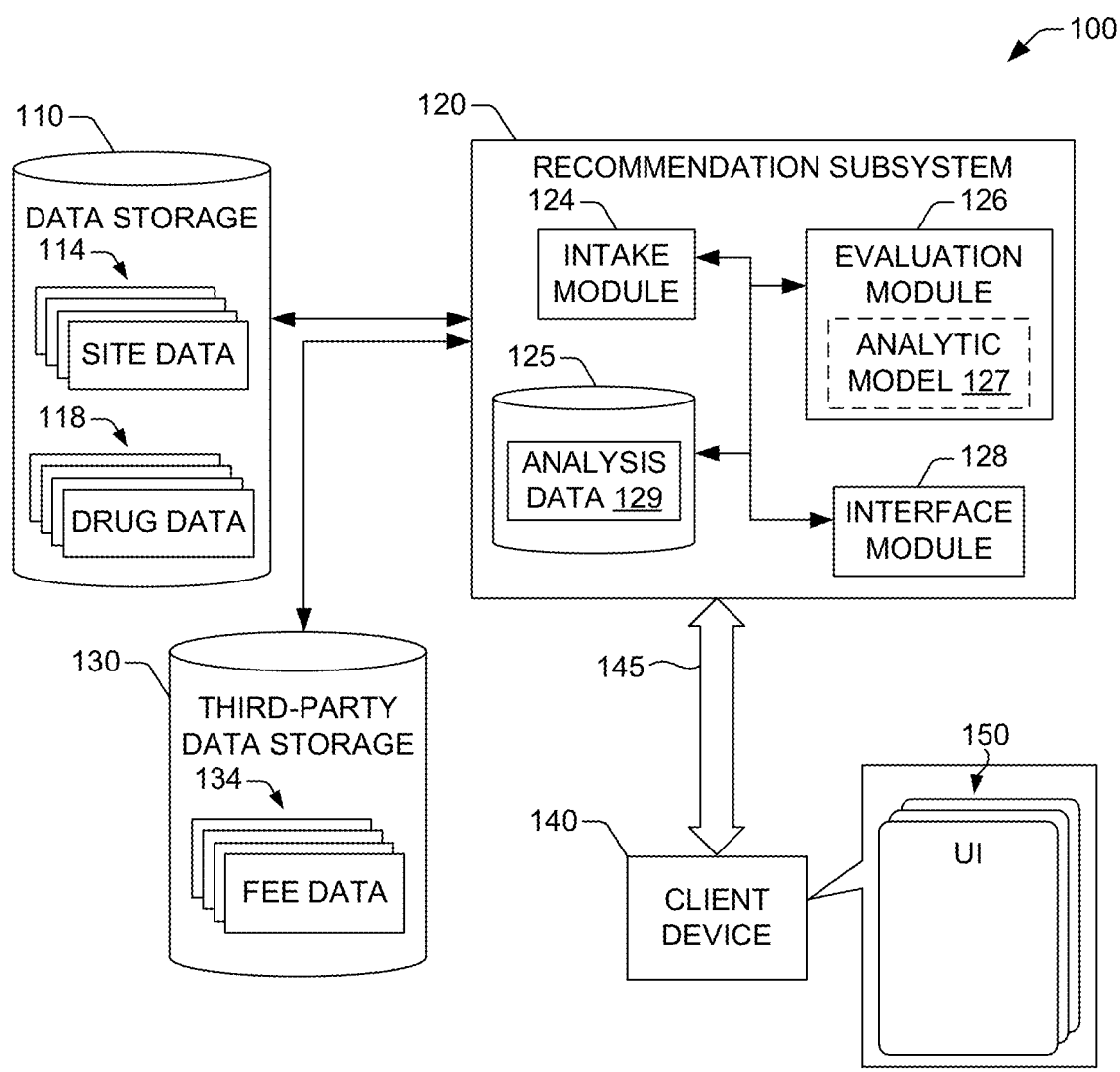
FIG. 1 illustrates an example of a computing system for COT recommendations for healthcare sites, in accordance with one or more embodiments of this disclosure.

FIG. 1 schematically illustrates an example of a computing system 100 for providing recommendation for COT for a healthcare site, in accordance with one or more embodiments of this disclosure. The computing system 100 includes one or more memory devices 110 (generically referred to as data storage 110) containing various types of site data 114. The site data 114 includes historical data defining values of operational attributes of a healthcare site. The historical data corresponds to historical time period of operation of the healthcare site. The historical time period can span three months, six months, nine months, or 12 months, for example. A first group of the operational attributes corresponds to a drug acquisition category. That group can include multiple first attributes, such as type of drug, name of drug, amount of drug. Thus, first data of the historical data can define values of the multiple first attributes. A second group of operational attributes corresponds to a procedure category. The second group of attributes can include multiple second attributes, such as physician identifier (ID), procedure date, procedure code, and procedure fee.

The computing system 100 also includes a recommendation subsystem 120 that can use the site data 114 to generate a recommendation for COT for the healthcare site. The recommendation subsystem 120 includes an intake module 124 that can access at least a portion of the site data 114. The site data 114 that is accessed includes first historical data defining values of operational attributes corresponding to the drug acquisition category, and second historical data defining values of operational attributes corresponding to the procedure category. The intake module 124 can access data in numerous ways.

The intake module 124 can access other data that can be used to generate cost data and reimbursement data. That other data can be accessed from one or both of the data storage 110 or one or more third-party memory devices 130 (generically referred to as third-party data storage 130). That other data can include drug data 118 (such as drug pricing data) and fee data 134 defining fee schedules. The fee data 134 defining fee schedules can include first data defining a fee schedule appropriate for operation under a first COT and second data defining a fee schedule appropriate for operation under a second COT. For example, the first COT can be Hospital COT and the second COT can be Clinic COT. As is illustrated in FIG. 1, the intake module 124 can access the drug data 118 from the data storage 110, and the fee data 134 from the third-party data storage 130. The fee data 134 includes the first data and the second data.

A third-party platform hosts the third-party data storage 130. The third-party platform can be a government platform or a private enterprise platform. The government platform can be embodied in, or can include, a computing platform administered by Medicare, for example. The private enterprise platform can be embodied in, or can include, a computing platform administered by a health insurance company or another type of commercial payer, for example. In some cases, the intake module 124 can access the fee data 134 programmatically by executing a function call that is part of an application programming interface (API) provided by the third-party platform. In other cases, the intake module 124 can execute defined program code (a bot, for example) to obtain the fee data 134. For example, execution of the bot can cause the intake module 124 to download one or several files containing the fee data 134 from the third-party data storage 130. In addition, or in some cases, execution of the defined program code (e.g., the bot) also can cause the intake module 124 to obtain other fee data that can supplement the fee data 134. Although not depicted in FIG. 1, that other fee data can be obtained from the data storage 110, for example. In some scenarios, the intake module 124 can combine the fee data 134 and the other fee data.

The intake module 124 can send the various data that have been accessed—e.g., site data 114, drug data 118, and fee data 134—to an evaluation module 126 included in the recommendation subsystem 120. The evaluation module 126 can determine, based on the data received by the evaluation module 126, a performance metric for the healthcare site according to a first COT (e.g., Hospital COT). Also based on such data, the evaluation module 126 can determine the same performance metric for the healthcare site according to a second COT. Determining the performance metric includes determining a value of the performance metric. The performance metric can be the net change in operating cost and reimbursement for the healthcare site over the historical time interval.

Because fee schedules defined by the fee data 134 that is accessed may not directly present a one-to-one relationship with procedure codes relied upon by the healthcare site, the evaluation module 126 can apply an analytic model 127 to one or more of the fee schedules accessed via the intake module 124. As mentioned, the accessed fee data 134 define the fee schedule(s). The analytic model 127 can be applied prior to determining the performance metric. In some cases, the analytic model 127 can be retained in the memory device(s) 125 and the evaluation module 126 can upload the analytic model 127. In other cases, the analytic model can be native to evaluation module 126. By applying the analytic model 127 to a fee schedule, a transformation is applied to the fee schedule, where the transformation creates a one-to-one relationship between fee codes and procedure codes irrespective of COT. In other words, that transformation can normalize the fee schedule or the data defining procedure codes, or both, in order to permit a uniform comparison between data under different classes of trade. More specifically, in some cases, the analytic model 127 can include one or more rules that, when applied to procedure codes across different COTs, can determine differences in structure among fee schedules for those COTs. Application of the analytic model 127 also can yield reason codes describing a reason (or explanation) for a difference to be present or absent. The analytic model 127 can identify procedure codes for which such differences are present and can then reconcile those differences. Reconciling the differences can include, for example, applying appropriate offsets to respective fee amounts for procedure codes across COT. In some cases, a group of multiple procedure categories can be used to reconcile differences in structure among fee schedules for respective COTs. The analytic model 127 can include, in one or more rules, for example, the group of multiple procedure categories and can use such categories to determine if differences in fee structure are present. After the group of multiple procedure categories has been implemented in such a fashion, the evaluation module 126 can further apply the analytic model 127 to at least some of the fee data 134 on a per-procedure basis.

The evaluation module 126 can then solve a binary recommendation task to identify one of the first COT or the second COT as a recommended COT for the healthcare site. Solving the binary recommendation task can include generating respective weights (which can be signed) for the first COT and the second COT, and then selecting the class of trade that has the greater weight. A weight can represent a fitness of a COT to the historical operating attributes of a healthcare site. The first weight assigned to the first COT can be the performance metric according to the first COT. The second weight assigned to the second COT can be the second performance metric according to the second COT. Accordingly, the evaluation module 126 can generate, based on the performance metric and the second performance metric, a recommendation to configure the healthcare site according to one of the first COT or the second COT. The evaluation module 126 can retain the recommendation in one or more memory devices 125, as part of analysis data 129 generated as part of generating such a recommendation.

The recommendation subsystem 120 also includes an interface module 128 that can supply the recommendation for COT for the healthcare site and data pertaining to the underlying analysis that yields such a recommendation. The interface module 128 may supply the recommendation and data to a client device 140. More specifically, the interface module 128 can cause or otherwise direct the client device 140 to present the recommendation for COT for a healthcare site. The interface module 128 also can cause the client device 140 to present various data views of the analysis data 129 pertaining to the underlying analysis that yields such a recommendation. The client device 140 may be embodied in, for example, a server device, a personal computer (PC), a laptop computer, a tablet computer, or a smartphone.

The recommendation for COT for the healthcare site and the data pertaining to the underlying analysis that yields the recommendation may be supplied in numerous ways. As an example, the interface module 128 can send data indicative of the recommendation and that other data to the client device 140 via a network(s) 145 (represented by an open arrow in FIG. 1). The network(s) 145 may comprise wired link(s) and/or wireless link(s) and several network elements (such as routers or switches, concentrators, servers, and the like) that form a communication architecture having a defined footprint. The network(s) 145 may be embodied in a local area network (LAN), a metropolitan area network (MAN), a wide area network (WAN), or a combination thereof. As another example, the interface module 128 may retain the data indicative of the recommendation for COT for the healthcare site and the other data in one or more memory devices (not depicted in FIG. 1) and can configure an interface (such as an API) to permit access to the stored data via a function call. The client device 140 can programmatically access the data indicative of the recommendation and the other data by executing the function call.

The client device 140 can interact with the recommendation subsystem 120 to access a recommendation and/or various data views of the analysis data 129 pertaining to the underlying analysis that yields the recommendation. The client device 140 is functionally coupled to a computing platform that includes the recommendation subsystem 120. In some cases, the client device 140 is part of that computing platform and can provide (e.g., present) the recommendation and/or the various data views to a third-party user device. In other cases, the client device 140 can be part of a third-party platform and can have access rights that determine a scope of access to the recommendation and/or the various data views. The computing platform that includes the recommendation subsystem 120 can configure the access rights for the client device 140.

To interact with the recommendation subsystem 120, the client device 140 can present one or more user interfaces 150. A display device integrated into or functionally coupled to the client device 140 can present the one or more user interfaces 150. The user interface(s) 150 can be presented at the direction of the interface module 128, and include selectable visual elements that permit controlling, at least partially, the presentation of one or more of the various data views. Selection of at least one of the selectable UI element(s) can permit interacting with the recommendation subsystem 120. More specifically, selection of a selectable UI element can cause the client device 140 to send request data to the interface module 128. The request data can be sent via the network(s) 145. In response to receiving the request data, the interface module 128 can send data defining a data view of one or multiple elements of the of the analysis data 129 pertaining to the analysis underlying the recommendation.

The user interfaces 150 can be presented individually or in a particular combination of two or more user interfaces. A first user interface (UI) of the user interfaces 150 can present a summary view that includes the recommendation for COT for the healthcare site. The summary view also can include UI elements identifying respective performance metrics of operation of the healthcare site relative to another COT different from the recommended COT. In one example, the recommended COT is Clinic COT and the other COT is Hospital COT, and a performance metric can be the net improvement in cost and reimbursement at Clinic COT relative to Hospital COT.

The first user interface also includes multiple selectable UI elements that can control, at least partially, presentation of other data views conveying insights from the of the analysis data 129 pertaining to the analysis that yields the recommended COT. Selection of a first selectable UI element of the multiple selectable UI elements can cause presentation of a particular group of one or more data views. Selection of a second selectable UI element of the multiple selectable UI elements can permit navigating to a portal that provides resources for configuration of the healthcare site according to the recommended COT.

Figure 3A:
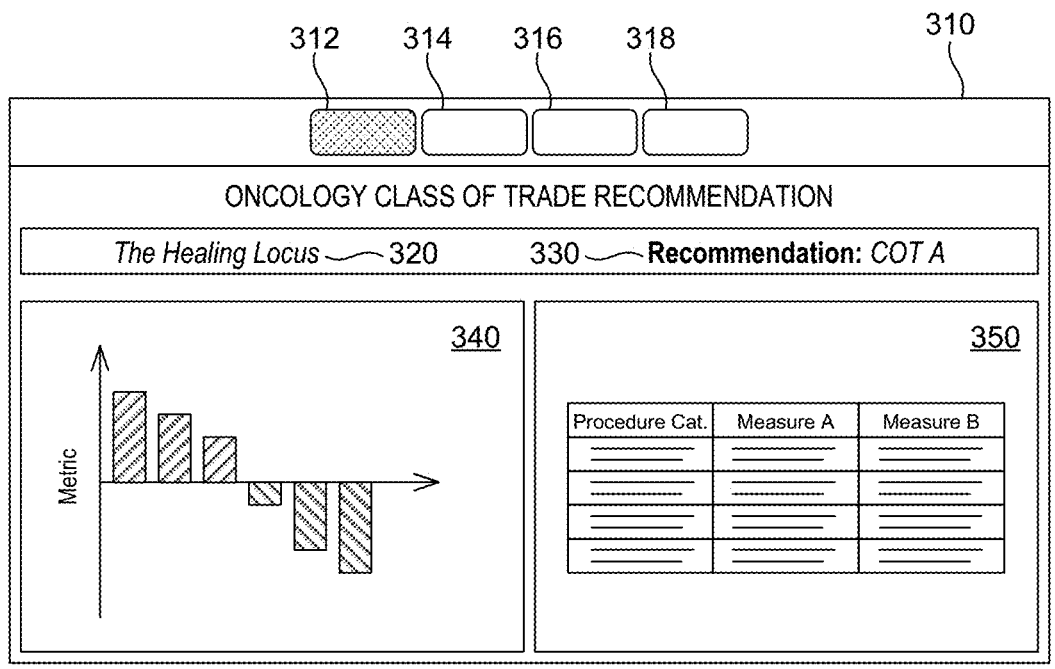
FIG. 3A illustrates an example of a user interface, in accordance with one or more embodiments of this disclosure.

An example of the first user interface is the user interface 310 shown in FIG. 3A. The user interface 310 presents a summary view including an identifier (ID) 320 of a healthcare site. The ID 220 uniquely identifies the healthcare site within the recommendation subsystem 120. The ID 320 can be human-readable, in some cases. For example, the ID 320 can be a name of the healthcare site. In other cases, the ID 320 can be a combination of such a name and an alphanumeric code. The alphanumeric code can be a universally unique identifier (UUID). The user interface 310 also presents a UI element 330 indicative of the recommendation for COT. The UI element 330 can include text indicative of the recommendation for COT (denoted by "COT A" in the UI 310). The text can have a format (e.g., font size, font type, and/or color) that conspicuously conveys the recommendation for COT.

The user interface 310 also includes a chart 340 conveying a data view of the analysis data 129 pertaining to the analysis underlying the recommendation for COT. The chart 340 can be formatted in way that conspicuously conveys information within the data view. Simply for the sake of illustration, the chart 340 is represented by a bar chart conveying a measure (e.g., gain or loss) as a function of a dimension or field (such as a drug name/type) that is part of the data view. The user interface also includes and a table 350 conveying another data view of data pertaining to that analysis. Simply for the sake of illustration, the table 350 is represented by a procedure category field and two measures (denoted by "Measure A" and "Measure B"). A first one of the two measures can be a quantity of procedures, and a second one of the two measures can be reimbursement impact. For purposes of illustration, the reimbursement impact can be a gain or a loss at the recommended COT relative to another COT.

The user interface 310 further includes multiple selectable UI elements, including a first selectable UI element 312, a second selectable UI element 314, a third selectable UI element 316, and a fourth selectable UI element 318. The multiple selectable UI elements can be embodied in selectable blocks or selectable tabs, for example. Selection of the first selectable UI element 312 causes the client device 140 to present the summary view shown in FIG. 3A. Selection of the second selectable UI element 314 can cause the client device 140 to present another UI including one or more charts, one or more tables, or a combination thereof, representing a defined data view. For example, that other UI can present a chart showing data indicative of drug expenditure according to drug manufacturer. Selection of the third selectable UI element 316 can cause the client device 140 to present information indicative of channel optimization. Such a channel optimization can include incorporating alternative drug suppliers, for example, into the underlying analysis that yield a COT recommendation. To that point, in some cases, selection of the third selectable UI element 316 can cause the evaluation module 126 to generate a second recommendation including alternative drug supplied in the analysis. Selection of the fourth selectable UI element 318 can cause the client device 140 to present another UI (not depicted in FIG. 3A) including information indicative of internal aspects of the analysis underlying the recommendation for COT (e.g., "COT A"). That information can include, for example, a description of the application of the analytic model 127 to the fee data 134, as part of the generation of the recommendation for COT. The analytic model 127 may include a parse function that can select first procedure code(s) to be excluded from and/or second procedure codes to be included in the analysis underlying the recommendation for COT. Thus, such a description can include an explanation of the parsing functionality and application thereof in the analysis. The description also can include another explanation of reason(s) for inclusion or exclusion of a particular procedure code.

Figure 3B:
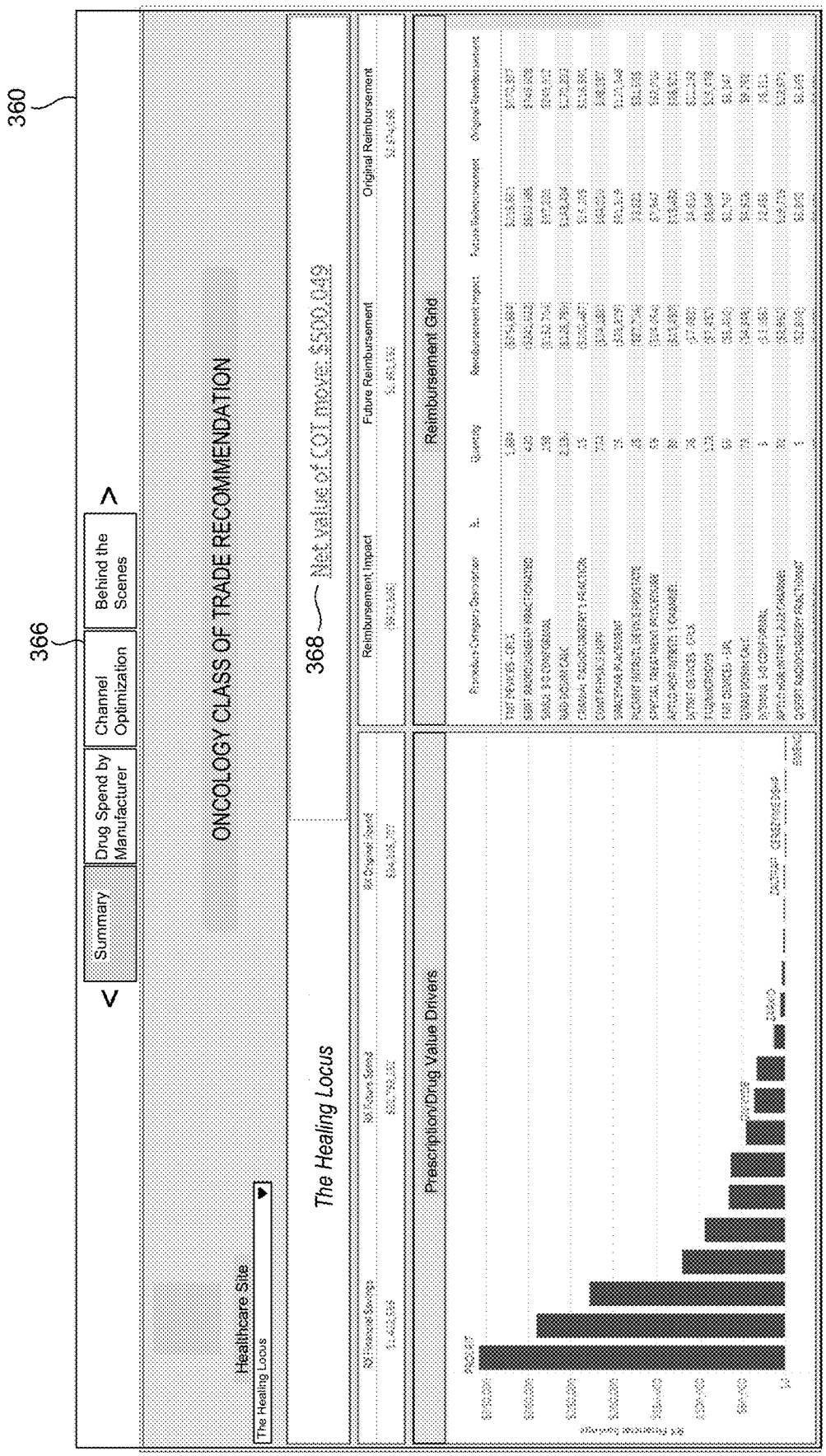
FIG. 3B illustrates another example of a user interface, in accordance with one or more embodiments of this disclosure.
Figure 3C:
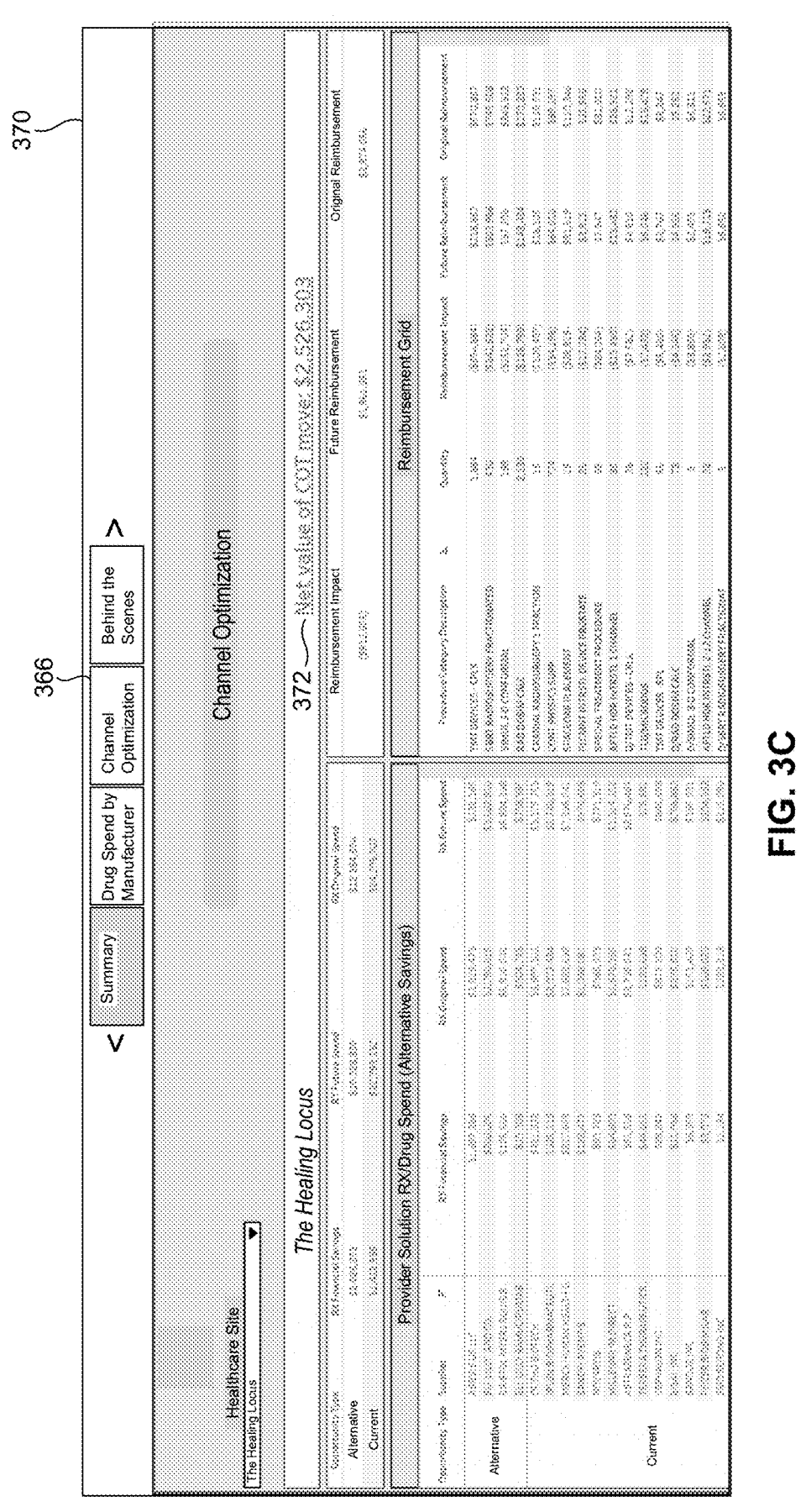

The UI 360 shown in FIG. 3B is an example of the summary view shown in UI 310 (FIG. 3A). It is noted that a COT recommendation 368 is presented in terms of a net gain resulting from transition a healthcare site to the recommended COT. The UI 370 shown in FIG. 3C is an example of the UI that the client device 140 can present in response to selection of the selectable UI element 362 in the UI 360. It is noted that a COT recommendation 372 is presented in terms of a net gain resulting from transition a healthcare site to the recommended COT, which can incorporate the effects of relying on alternative drug suppliers are contemplated.

Figure 2:
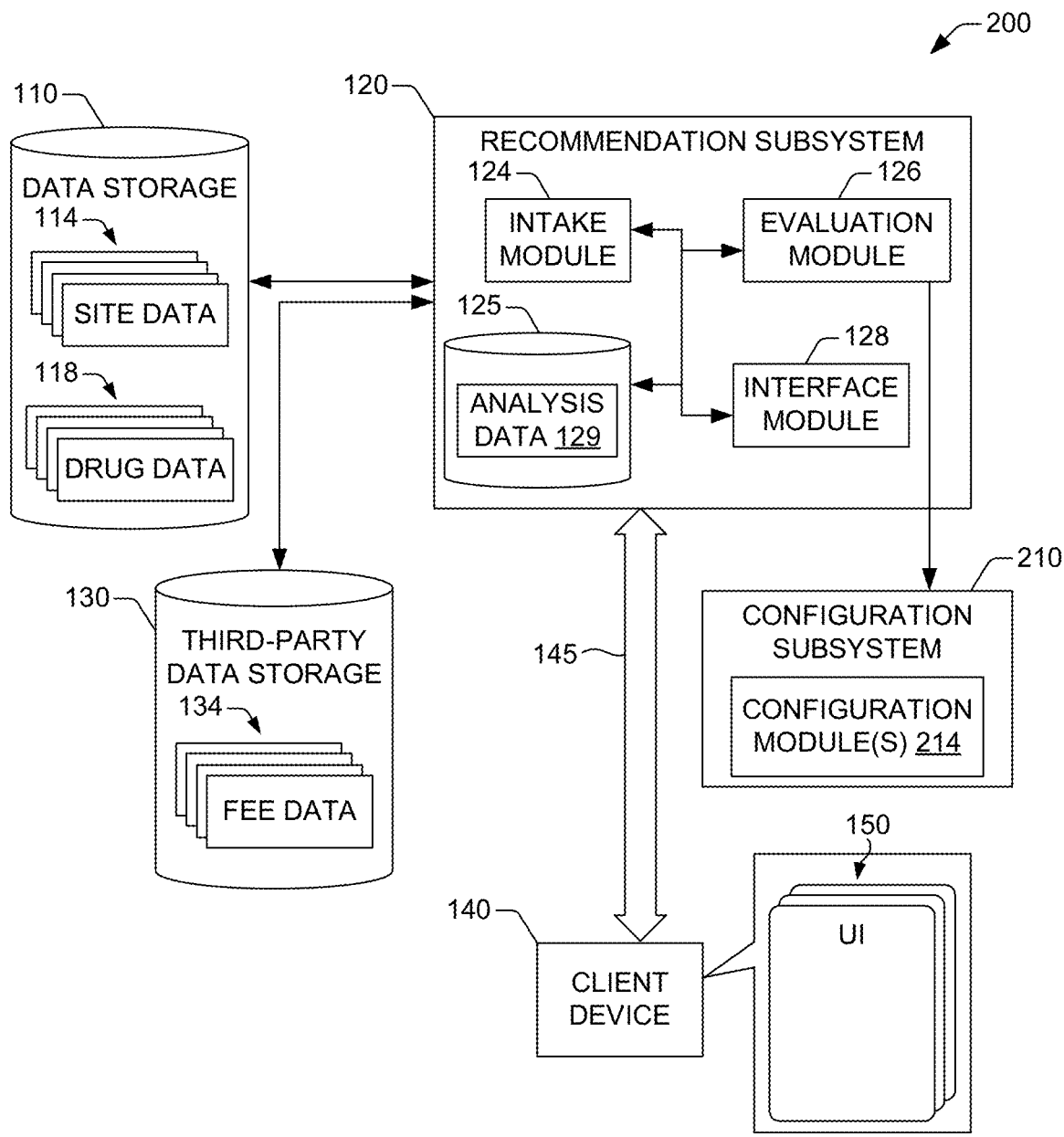
FIG. 2 illustrates another example of a computing system for COT recommendations for healthcare sites, in accordance with one or more embodiments of this disclosure.

In some embodiments, as is shown in FIG. 2, a computing system 200 can include a configuration subsystem 210 that can receive a recommendation for COT for a healthcare site (e.g., oncology practice, rheumatology practice, or neurology practice) and can configure various computational resources to simplify the implementation of configuration of a healthcare site according to a recommended COT. To that point, the configuration subsystem 210 can mount a file system for the healthcare site, where various files involved in the configuration of the healthcare site can be centralized. In addition, or in some cases, the configuration subsystem 210 can generate a website or another type of web-based workspace where resources related to the configuration of the healthcare site can be made accessible to the client device 140 and/or other devices. The configuration subsystem 210 can provide, or otherwise include, one or more communication channels within that workspace in order to permit communication between an agent of the healthcare site and a support agent. An example of a communication channel can be embodied in, or can include, a user interface having one or multiple selectable UI elements. Selection of a particular UI element of the selectable UI element(s) can permit communication via chat session, voice call, or email. The configuration subsystem 210 also can allocate storage within storage resources (e.g., on-site storage server device(s) and/or cloud-based storage server device(s)) available to the recommendation subsystem 120. That storage can retain various types of records related to a transition of the healthcare site to the recommended COT. The configuration subsystem 210 can include one or multiple configuration modules 214 that, individually or in combination, can implement the described functionality of the configuration subsystem 210.

Figure 3D:
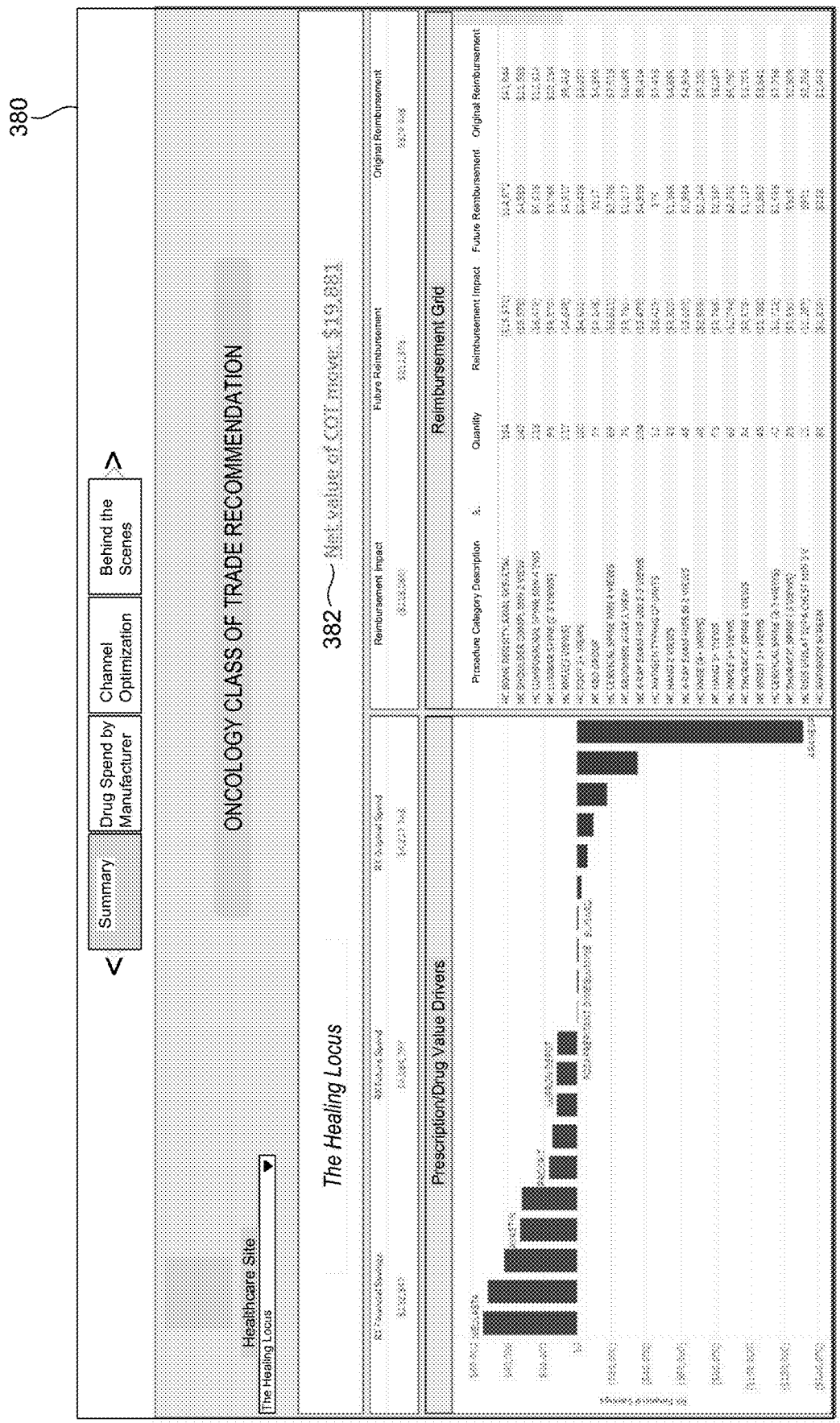
FIG. 3D illustrates another example of a user interface, in accordance with one or more embodiments of this disclosure.

The generation of a recommendation for COT for a particular healthcare site need not be implemented a single time. Indeed, the recommendation subsystem 120 can generate a recommendation for COT dynamically, in response to a particular condition (such as a defined state of operations of the healthcare site) being satisfied, or periodically at defined time intervals (e.g., every three months, six months, or 12 months). To that end, after a recommendation for COT has been generated, the intake module 124 can continue accessing site data, drug data, and fee data over time, from the data storage 110, for example, and can monitor the particular condition to determine if the particular condition has been satisfied. In addition, or in some cases, the evaluation module 126 can monitor a current time to determine if a recommendation for COT is to be generated. The magnitude of a time interval and/or a condition relied upon to determine if a recommendation for COT is to be generated can be configurable. The intake module 124 can receive, at one or several times, configuration data (not depicted in FIG. 1 or FIG. 2) defining such a time interval or condition, or both. Simply for purposes of illustration, at a time after the analysis that to generate the COT recommendation 368 summarized by UI 360 (FIG. 3B), the recommendation subsystem 120 can generate a second COT recommendation for the same healthcare site (denoted as "The Healing Locus," merely for the sake of nomenclature). In response, the client device 140 can present the UI 380 shown in FIG. 3D, summarizing the second COT recommendation 382. It is noted that the COT recommendation 382 is presented in terms of a net gain resulting from transition the healthcare site to the recommended COT.

By generating recommendations for COT periodically, for example, the evaluation module 126 can generate a time series of a performance metric for a particular COT for a healthcare site. In some embodiments, instead of relying on the evaluation module 126 for forecasting functionality, the recommendation subsystem 120 can include a predictor module (not depicted in FIG. 1 or FIG. 2) that can apply regression techniques and/or other types of unsupervised machine-learning techniques to the time series. As a result, the predictor module can predict values of the performance metric at future times. Based on predictions of respective values of a first performance metric for a first COT and a second performance metric for a second COT for a healthcare site at a future time, the evaluation module 126 can generate a prospective recommendation for COT at the future time.

Further, as part of the generation of such performance metrics over time, the predictor module can generate numerous insights at various times that can reveal predicted changes to site data that yield particular values of the performance metrics. That is, the predictor module can provide predicted time dependence of elements of operation of a healthcare site, such as temporal changes in the number of a particular procedure corresponding to a procedure code.

Further, besides utilizing ground-truth site data and ground-truth drug data, the recommendation subsystem 120 can generate a recommendation for COT for a healthcare site based on synthetic data. As mentioned, in some embodiments, the recommendation subsystem 120 can include a predictor module (not depicted in FIG. 1 or FIG. 2). The predictor module can generate a synthetic time series of site data and drug data for the healthcare site, for a defined time period. There are numerous ways to generate such synthetic time series. In some cases, the predictor module can identify a second healthcare site that is similar to the healthcare site, where that second healthcare site has supplied ground-truth site data and ground-truth drug data. The predictor module can generate the synthetic time series by applying a defined transform to such ground-truth data. In addition, or in other cases, the predictor module can use a generative adversarial network (GAN) to generate the synthetic time series. The evaluation module 126 can then generate a recommendation for COT based on the synthetic time series and fee data 134. As a result the recommendation subsystem 120 may predict a time and/or condition in which a transition to a different COT is warranted. Such a prediction functionality can complement, for example, the other prediction functionality that is based on machine-learned time-dependency of performance metrics for respective COTs.

Figure 4:
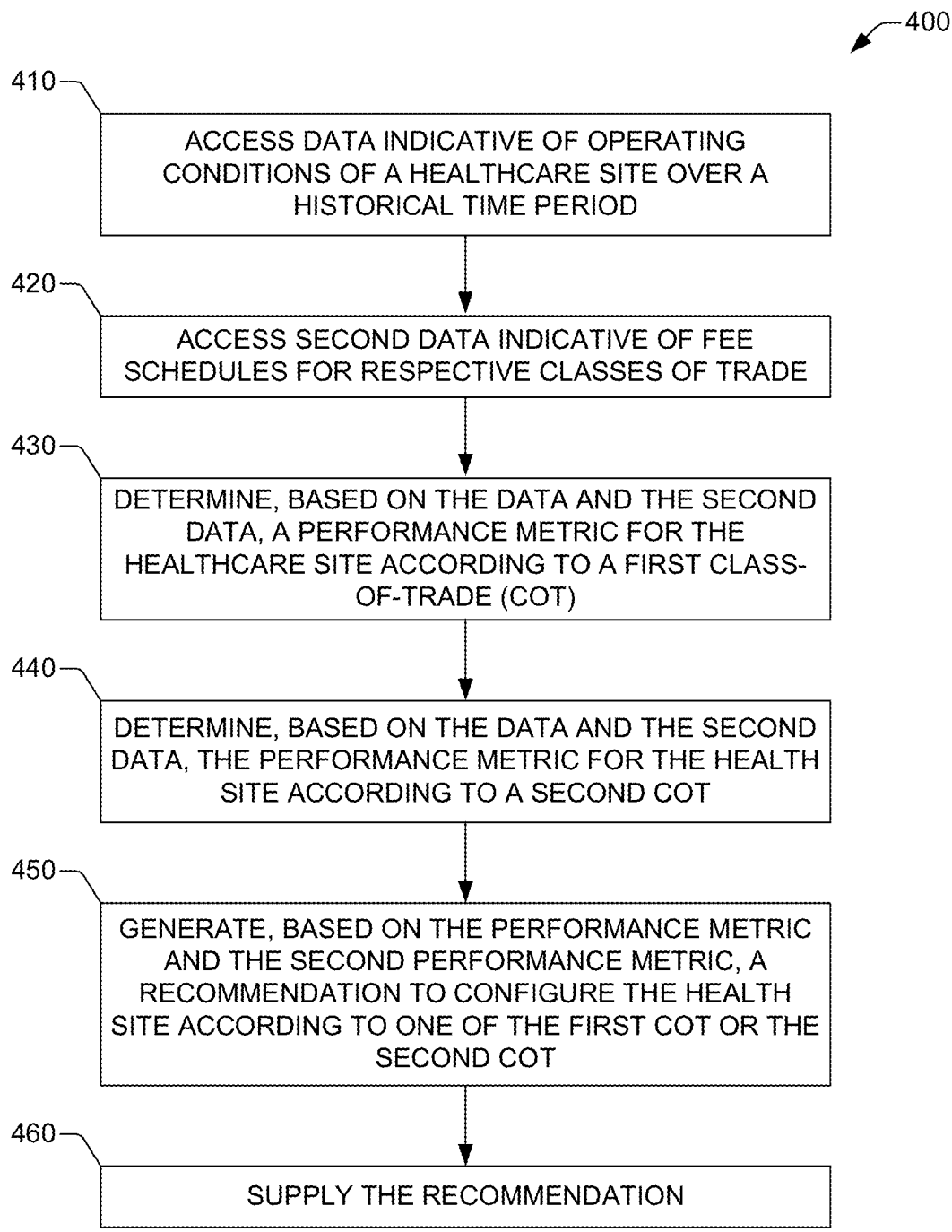
FIG. 4 illustrates an example of a method for providing a COT recommendation for a healthcare site, in accordance with one or more embodiments of this disclosure.

FIG. 4 is a flowchart of an example method 400 for providing a COT recommendation for a healthcare site, in accordance with one or more embodiments of this disclosure. A computing system can perform the example method 400 in its entirety or in part. To that end, the computing system includes computing resources that can implement at least one of the blocks included in the example method 400. The computing resources include, for example, central processing units (CPUs), graphics processing units (GPUs), tensor processing units (TPUs), memory, disk space, incoming bandwidth, and/or outgoing bandwidth, interface(s) (such as I/O interfaces or APIs, or both); controller devices (s); power supplies; a combination of the foregoing; and/or similar resources. For instance, the computing system can include programming interface(s); an operating system; software for configuration and or control of a virtualized environment; firmware; and similar resources. The computing system can embody, or can include, the recommendation subsystem 120 (FIG. 1) or both the recommendation subsystem 120 (FIG. 1) and the configuration subsystem 210 (FIG. 2).

At block 410, the computing system can access (via the intake module 124, for example) data indicative of an operating conditions of a healthcare site over a historical time period. The data can include first historical data defining values of operational attributes corresponding to a drug acquisition category, and second historical data defining values of operational attributes corresponding to a procedure category. The historical time period extends from a first time to a second time after the first time, where the second time is prior to or the same as a current time at which a COT assessment is performed. The time spanned from the first time to the second time can be, for example, three months, six months, nine months, or 12 months. In one example, the historical time period can span six consecutive months prior to a current time at which a COT assessment is performed.

At block 420, the computing system can access (via the intake module 124, for example) data indicative of fee schedules for respective classes of trade. As mentioned, in a binary recommendation task, accessing the data includes accessing first data indicative of a first fee schedule according to a first COT (e.g., Hospital COT), and also accessing second data indicative of a second fee schedule according to a second COT (Clinic COT).

At block 430, the computing system can determine, based on the data and the second data, a performance metric for the healthcare site according to (or operating under) a first COT. The performance metric can be determined via the evaluation module 126, for example.

At block 440, the computing system can determine, based on the data and the second data, a second performance metric for the healthcare site according to (or operating under) a second COT. The performance metric can be determined via the evaluation module 126, for example.

At block 450, the computing system generate (via the evaluation module 126, for example) a recommendation to configure the healthcare site according to one of the first COT or the second COT. The recommendation can be generated based on the performance metric and the second performance metric.

At block 460, the computing system can supply the recommendation. The recommendation can be supplied via the interface module 128, for example. In some cases, supplying the recommendation includes causing a computing device to present a user interface (UI) comprising a UI element indicative of the recommendation. The user also can include an identifier for the healthcare site, a chart conveying a first data view of the analysis data 129 associated with the recommendation, and/or a table conveying a second data view of the analysis data 129 associated with the recommendation. In addition, or in other cases, supplying the recommendation comprises configuring an application programming interface to permit accessing data indicative of the recommendation via a function call.

Figure 5:
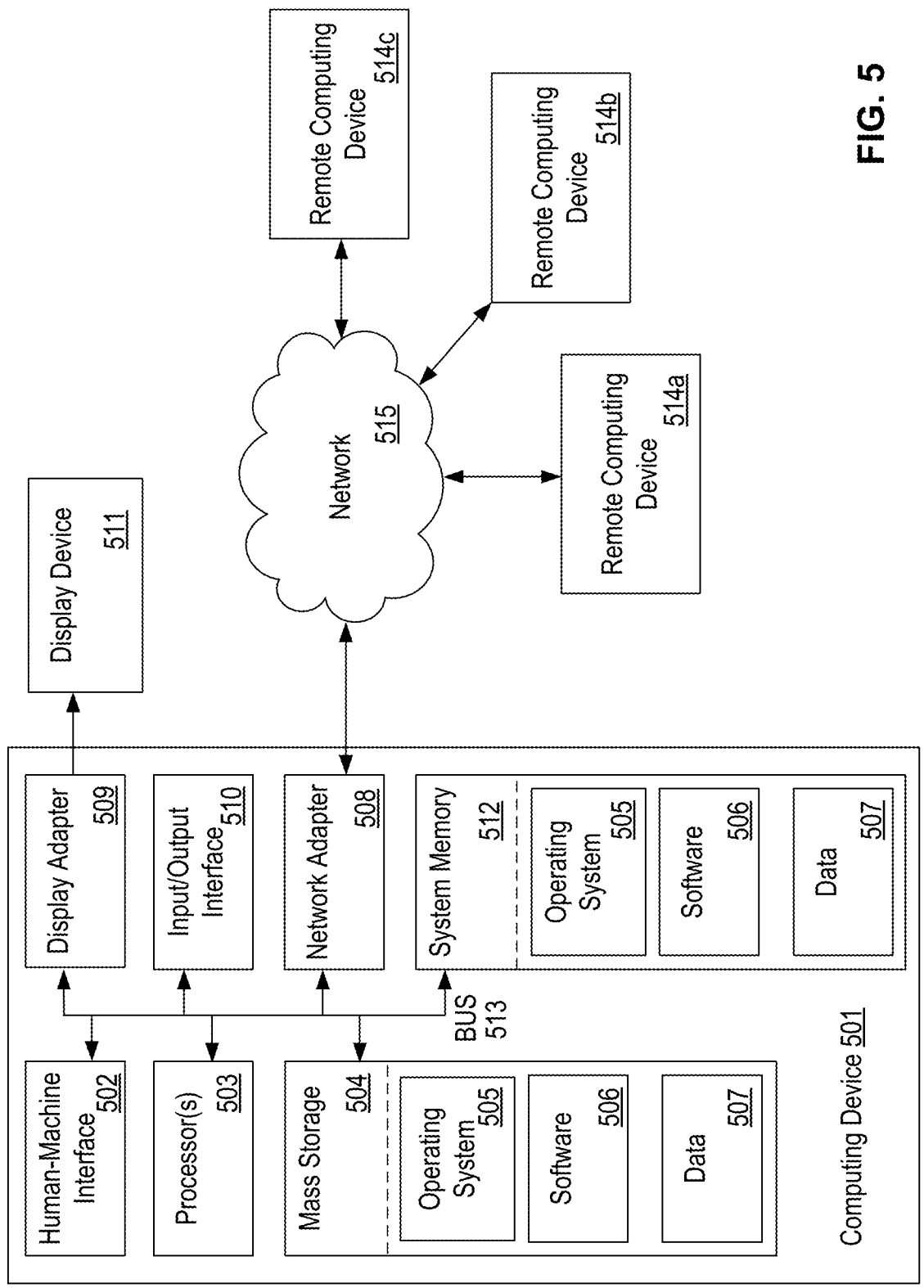
FIG. 5 illustrates an example of a computing system that can implement generation of COT recommendations for healthcare sites, in accordance with one or more embodiments of this disclosure.

In order to provide some context, the computer-implemented methods and systems of this disclosure can be implemented on the computing system illustrated in FIG. 5 and described below. Similarly, the computer-implemented methods and systems disclosed herein can utilize one or more computing devices to perform one or more functions in one or more locations. FIG. 5 is a block diagram illustrating an example of a computing system 500 for performing the disclosed methods and/or implementing the disclosed systems. The computing system 500 shown in FIG. 5 is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment. The computing system 500 shown in FIG. 5 can embody at least a portion of the computing system 100 (FIG. 1) and/or at least a portion of the computing system 200 (FIG. 2), and can implemented the various functionalities described herein connection with generation of a COT recommendation for a healthcare site.

The computer-implemented methods and systems in accordance with this disclosure can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set-top boxes, programmable consumer electronics, network PCs, minicomputers, mainframe computers, distributed computing environments that comprise any of the above systems or devices, and the like.

The processing of the disclosed computer-implemented methods and systems can be performed by software components. The software components can include, in some embodiments, the intake module 124 (FIG. 1), the evaluation module 126 (FIG. 1), and the interface module 128 (FIG. 1). In other embodiments, the software components can include such modules (which can be included in the recommendation subsystem 120) and other modules that constitute the configuration subsystem 210. The disclosed systems and computer-implemented methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed computer-implemented methods can also be practiced in grid-based and distributed computing environments where tasks are performed by remote processing devices that are linked through a communications network. In a distributed computing environment, program modules can be located in both local and remote computer storage media including memory storage devices.

Further, the systems and computer-implemented methods disclosed herein can be implemented via a general-purpose computing device in the form of a computing device 501. The components of the computing device 501 can comprise, but are not limited to, one or more processors 503, a system memory 512, and a system bus 513 that functionally couples various system components including the one or more processors 503 to the system memory 512. The system can utilize parallel computing.

The system bus 513 represents one or more of several possible types of bus structures, including a memory bus or memory controller, a peripheral bus, an accelerated graphics port, or local bus using any of a variety of bus architectures. The system bus 513, and all buses specified in this description can also be implemented over a wired or wireless network connection and each of the subsystems, including the one or more processors 503, one or more mass storage devices 504 (referred to as mass storage 504), an operating system 505, software 506, data 507, a network adapter 508, the system memory 512, an Input/Output Interface 510, a display adapter 509, a display device 511, and a human-machine interface 502, can be contained within one or more remote computing devices 514a,b,c at physically separate locations, connected through buses of this form, in effect implementing a fully distributed system. The software 506 can include, in some embodiments, the intake module 124 (FIG. 1), the evaluation module 126 (FIG. 1), and the interface module 128 (FIG. 1). In other embodiments, the software 506 can include such modules (which can be included in the recommendation subsystem 120) and the configuration module(s) 214 that constitute the configuration subsystem 210 (FIG. 2).

The computing device 501 typically comprises a variety of computer-readable media. Exemplary readable media can be any available media that is accessible by the computing device 501 and comprises, for example and not meant to be limiting, both volatile and non-volatile media, removable and non-removable media. The system memory 512 comprises computer readable media in the form of volatile memory, such as random access memory (RAM), and/or non-volatile memory, such as read only memory (ROM). The system memory 512 typically contains data such as the data 507 and/or program modules such as the operating system 505 and the software 506 that are immediately accessible to and/or are presently operated on by the one or more processors 503.

In another aspect, the computing device 501 can also comprise other removable/non-removable, volatile/non-volatile computer storage media. As an example, FIG. 5 illustrates the mass storage 504 which can provide non-volatile storage of computer code, computer readable instructions, data structures, program modules, and other data for the computing device 501. For example and not meant to be limiting, the mass storage 504 can be embodied in, or can include, a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EE-PROM), and the like.

Optionally, any number of program modules can be stored on the mass storage 504, including by way of example, the operating system 505 and the software 506. Each of the operating system 505 and the software 506 (or some combination thereof) can comprise elements of the programming and the software 506. The data 507 can also be stored on the mass storage 504. The data 507 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems. The data 507 can include, in some cases, analysis data 129 (including recommendations for COT), analytic models in accordance with aspects described herein (e.g., analytic model 127), and other data. In some embodiments, at least one remote device (e.g., one or more of remote device 514a, remote device 514b, or remote device 514c, can include site data 114 and/or drug data 118. In addition, or in some embodiments, one of the remote devices 514a,b,c can include fee data 134 instead of site data 114 and drug data 118.

In another aspect, the user can enter commands and information into the computing device 501 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the one or more processors 503 via the human-machine interface 502 that is coupled to the system bus 513, but can be connected by other interface and bus structures, such as a parallel port, game port, an IEEE 1394 Port (also known as a Firewire port), a serial port, or a universal serial bus (USB).

In yet another aspect, the display device 511 can also be connected to the system bus 513 via an interface, such as the display adapter 509. It is contemplated that the computing device 501 can have more than one display adapter 509 and the computing device 501 can have more than one display device 511. For example, the display device 511 can be a monitor, an LCD (Liquid Crystal Display), or a projector. In addition to the display device 511, other output peripheral devices can comprise components such as speakers (not shown) and a printer (not shown) which can be connected to the computing device 501 via the Input/Output Interface 510. Any operation and/or result of the methods can be output in any form to an output device. Such output can be any form of visual representation, including, but not limited to, textual, graphical, animation, audio, tactile, and the like. The display device 511 and computing device 501 can be part of one device, or separate devices.

The computing device 501 can operate in a networked environment using logical connections to one or more remote computing devices 514a,b,c. By way of example, a remote computing device can be a personal computer, portable computer, smartphone, a server, a router, a network computer, a peer device or other common network node, and so on. Logical connections between the computing device 501 and a remote computing device 514a,b,c can be made via a network 515, such as a local area network (LAN) and/or a general wide area network (WAN). Such network connections can be through the network adapter 508. The network adapter 508 can be implemented in both wired and wireless environments. In an aspect, one or more of the remote computing devices 514a,b,c can comprise an external engine and/or an interface to the external engine.

For purposes of illustration, application programs and other executable program components such as the operating system 505 are illustrated herein as discrete blocks, although it is recognized that such programs and components reside at various times in different storage components of the computing device 501, and are executed by the one or more processors 503 of the computer. An implementation of the software 506 can be stored on or transmitted across some form of computer-readable media. Any of the disclosed methods can be performed by computer readable instructions embodied on computer-readable media. Computer-readable media can be any available media that can be accessed by a computer. By way of example and not meant to be limiting, computer-readable media can comprise "computer storage media" and "communications media." "Computer storage media" comprise volatile and non-volatile, removable and non-removable media implemented in any methods or technology for storage of information such as computer-readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

It is to be understood that the computer-implemented methods and systems described here are not limited to specific operations, processes, components, or structure described, or to the order or particular combination of such operations or components as described. It is also to be understood that the terminology used herein is for the purpose of describing exemplary embodiments only and is not intended to be restrictive or limiting.

As used herein the singular forms "a," "an," and "the" include both singular and plural referents unless the context clearly dictates otherwise. Values expressed as approximations, by use of antecedents such as "about" or "approximately," shall include reasonable variations from the referenced values. If such approximate values are included with ranges, not only are the endpoints considered approximations, the magnitude of the range shall also be considered an approximation. Lists are to be considered exemplary and not restricted or limited to the elements comprising the list or to the order in which the elements have been listed unless the context clearly dictates otherwise.

Throughout the specification and claims of this disclosure, the following words have the meaning that is set forth: "comprise" and variations of the word, such as "comprising" and "comprises," mean including but not limited to, and are not intended to exclude, for example, other additives, components, integers, or operations. "Include" and variations of the word, such as "including" are not intended to mean something that is restricted or limited to what is indicated as being included, or to exclude what is not indicated. "May" means something that is permissive but not restrictive or limiting. "Optional" or "optionally" means something that may or may not be included without changing the result or what is being described. "Prefer" and variations of the word such as "preferred" or "preferably" mean something that is exemplary and more ideal, but not required. "Such as" means something that serves simply as an example.

Operations and components described herein as being used to perform the disclosed methods and construct the disclosed systems are illustrative unless the context clearly dictates otherwise. It is to be understood that when combinations, subsets, interactions, groups, etc. of these operations and components are disclosed, that while specific reference of each various individual and collective combinations and permutation of these may not be explicitly disclosed, each is specifically contemplated and described herein, for all methods and systems. This applies to all aspects of this application including, but not limited to, operations in disclosed methods and/or the components disclosed in the systems. Thus, if there are a variety of additional operations that can be performed or components that can be added, it is understood that each of these additional operations can be performed and components added with any specific embodiment or combination of embodiments of the disclosed systems and methods.

Embodiments of this disclosure may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. Any suitable computer-readable storage medium may be utilized including hard disks, CD-ROMs, optical storage devices, or magnetic storage devices, whether internal, networked, or cloud-based.

Embodiments of this disclosure have been described with reference to diagrams, flowcharts, and other illustrations of computer-implemented methods, systems, apparatuses, and computer program products. Each block of the block diagrams and flowchart illustrations, and combinations of blocks in the block diagrams and flowchart illustrations, respectively, can be implemented by processor-accessible instructions. Such instructions can include, for example, computer program instructions (e.g., processor-readable and/or processor-executable instructions). The processor-accessible instructions can be built (e.g., linked and compiled) and retained in processor-executable form in one or multiple memory devices or one or many other processor-accessible non-transitory storage media. These computer program instructions (built or otherwise) may be loaded onto a general-purpose computer, special purpose computer, or other programmable data processing apparatus to produce a machine. The loaded computer program instructions can be accessed and executed by one or multiple processors or other types of processing circuitry. In response to execution, the loaded computer program instructions provide the functionality described in connection with flowchart blocks (individually or in a particular combination) or blocks in block diagrams (individually or in a particular combination). Thus, such instructions which execute on the computer or other programmable data processing apparatus create a means for implementing the functions specified in the flowchart blocks (individually or in a particular combination) or blocks in block diagrams (individually or in a particular combination).

These computer program instructions may also be stored in a computer-readable memory that can direct a computer or other programmable data processing apparatus to function in a particular manner, such that the instructions stored in the computer-readable memory produce an article of manufacture including processor-accessible instruction (e.g., processor-readable instructions and/or processor-executable instructions) to implement the function specified in the flowchart blocks (individually or in a particular combination) or blocks in block diagrams (individually or in a particular combination). The computer program instructions (built or otherwise) may also be loaded onto a computer or other programmable data processing apparatus to cause a series of operations to be performed on the computer or other programmable apparatus to produce a computer-implemented process. The series of operations can be performed in response to execution by one or more processor or other types of processing circuitry. Thus, such instructions that execute on the computer or other programmable apparatus provide operations for implementing the functions specified in the flowchart blocks (individually or in a particular combination) or blocks in block diagrams (individually or in a particular combination).

Accordingly, blocks of the block diagrams and flowchart illustrations support combinations of means for performing the specified functions in connection with such diagrams and/or flowchart illustrations, combinations of operations for performing the specified functions and program instruction means for performing the specified functions. Each block of the block diagrams and flowchart illustrations, and combinations of blocks in the block diagrams and flowchart illustrations, can be implemented by special purpose hardware-based computer systems that perform the specified functions or operations, or combinations of special purpose hardware and computer instructions.

The methods and systems can employ artificial intelligence techniques such as machine learning and iterative learning. Examples of such techniques include, but are not limited to, expert systems, case-based reasoning, Bayesian networks, behavior-based AI, neural networks, fuzzy systems, evolutionary computation (e.g. genetic algorithms), swarm intelligence (e.g. ant algorithms), and hybrid intelligent systems (e.g. expert inference rules generated through a neural network or production rules from statistical learning).

While the computer-implemented methods, apparatuses, devices, and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its operations be performed in a specific order. Accordingly, where a method claim does not actually recite an order to be followed by its operations or it is not otherwise specifically stated in the claims or descriptions that the operations are to be limited to a specific order, it is in no way intended that an order be inferred, in any respect. This holds for any possible non-express basis for interpretation, including: matters of logic with respect to arrangement of operations or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:
1. A computing system, comprising:
at least one processor; and
at least one memory device having processor-executable instructions stored thereon that, in response to execution by the at least one processor, cause the computing system to:
access site data indicative of operating conditions of a healthcare site over a historical time period;
access drug pricing data indicative of fee schedules corresponding to respective classes of trade, wherein the fee schedules include first fee schedule data defining a fee schedule appropriate for operation under a first class of trade (COT) and second fee schedule data defining a fee schedule appropriate for operation under a second COT;
identify a second healthcare site that is similar to the healthcare site, wherein the second healthcare site is associated with ground-truth site data and ground-truth drug pricing data;
generate, via a generative adversarial network (GAN), synthetic site data and synthetic drug pricing data for the healthcare site, wherein the GAN generates the synthetic site data and the synthetic drug pricing data based on the site data, the drug pricing data, the ground-truth site data, and the ground-truth drug pricing data;

determine, based on: the fee schedules, the synthetic site data, and the synthetic drug pricing data, a first performance metric for the healthcare site according to the first COT;

determine, based on: the fee schedules, the synthetic site data, and the synthetic drug pricing data, a second performance metric for the healthcare site according to the second COT;

generate, based on the first performance metric and the second performance metric, a recommendation to configure the healthcare site according to one of the first COT or the second COT; and supply the recommendation, wherein the recommendation is indicative of one of more of: a time or condition for transitioning the healthcare site to a different COT.

2. The computing system of claim 1, wherein the first COT is a Hospital COT and the second COT is a Clinic COT, and wherein the historical time period spans one of three months, six months, or 12 months.

3. The computing system of claim 1, wherein determining the first performance metric comprises applying an analytic model to one or more of the synthetic site data or the synthetic drug pricing data to normalize the synthetic site data or the synthetic drug pricing data.

4. The computing system of claim 1, wherein supplying the recommendation comprises causing a computing device to present a user interface (UI) comprising a UI element indicative of the recommendation.

5. The computing system of claim 4, wherein the user interface further comprises at least one of an identifier for the healthcare site, a chart conveying a first data view associated with the recommendation, or a table conveying a second data view associated with the recommendation.

6. The computing system of claim 1, wherein supplying the recommendation comprises configuring an application programming interface (API) to permit accessing data indicative of the recommendation.

7. The computing system of claim 1, wherein accessing the drug pricing data comprises accessing a third-party data storage hosted by a third-party platform.

8. The computing system of claim 1, the at least one memory device having further processor-executable instructions stored thereon that in response to execution by the at least one processor further cause the computing system to update the recommendation periodically.

9. The computing system of claim 1, the at least one memory device having further processor-executable instructions stored thereon that in response to execution by the at least one processor further cause the computing system to update the recommendation based on a defined update condition being satisfied.

10. A computer-implemented method comprising:

accessing site data indicative of operating conditions of a healthcare site over a historical time period;

accessing drug pricing data indicative of fee schedules corresponding to respective classes of trade, wherein the fee schedules include first fee schedule data defining a fee schedule appropriate for operation under a first class of trade (COT) and second fee schedule data defining a fee schedule appropriate for operation under a second COT;

identifying a second healthcare site that is similar to the healthcare site, wherein the second healthcare site is associated with ground-truth site data and ground-truth drug pricing data;

generating, via a generative adversarial network (GAN), synthetic site data and synthetic drug pricing data for the healthcare site, wherein the GAN generates the synthetic site data and the synthetic drug pricing data based on the site data, the drug pricing data, the ground-truth site data, and the ground-truth drug pricing data;

determining, based on: the fee schedules, the synthetic site data, and the synthetic drug pricing data, a first performance metric for the healthcare site according to the first COT;

determining, based on: the fee schedules, the synthetic site data, and the synthetic drug pricing data, a second performance metric for the healthcare site according to the second COT;

generating, based on the first performance metric and the second performance metric, a recommendation to configure the healthcare site according to one of the first COT or the second COT; and supplying the recommendation, wherein the recommendation is indicative of one of more of: a time or condition for transitioning the healthcare site to a different COT.

11. The computer-implemented method of claim 10, wherein the supplying the recommendation comprises causing a computing device to present a user interface (UI) comprising a UI element indicative of the recommendation.

12. The computer-implemented method of claim 11, wherein the user interface further comprises at least one of an identifier for the healthcare site, a chart conveying a first data view associated with the recommendation, or a table conveying a second data view associated with the recommendation.

13. The computer-implemented method of claim 10, wherein the supplying the recommendation comprises configuring an application programming interface to permit accessing data indicative of the recommendation via a function call.

14. The computer-implemented method of claim 10, wherein the accessing the drug pricing data comprises accessing a third-party data storage hosted by a third-party platform.

15. The computer-implemented method of claim 10, further comprising updating the recommendation periodically.

16. The computer-implemented method of claim 10, further comprising updating the recommendation based on a defined update condition being satisfied.

17. At least one computer-readable non-transitory storage medium having processor-executable instructions stored thereon that, in response to execution, cause a computing system to:

access site data indicative of operating conditions of a healthcare site over a historical time period;

access drug pricing data indicative of fee schedules corresponding to respective classes of trade, wherein the fee schedules include first fee schedule data defining a fee schedule appropriate for operation under a first class of trade (COT) and second fee schedule data defining a fee schedule appropriate for operation under a second COT;

identify a second healthcare site that is similar to the healthcare site, wherein the second healthcare site is associated with ground-truth site data and ground-truth drug pricing data;

generate, via a generative adversarial network (GAN), synthetic site data and synthetic drug pricing data for the healthcare site, wherein the GAN generates the synthetic site data and the synthetic drug pricing data based on the site data, the drug pricing data, the ground-truth site data, and the ground-truth drug pricing data;

determine, based on: the fee schedules, the synthetic site data, and the synthetic drug pricing data, a first performance metric for the healthcare site according to the first COT;

determine, based on: the fee schedules, the synthetic site data, and the synthetic drug pricing data, a second performance metric for the healthcare site according to the second COT;

generate, based on the first performance metric and the second performance metric, a recommendation to configure the healthcare site according to one of the first COT or the second COT; and supply the recommendation, wherein the recommendation is indicative of one of more of: a time or condition for transitioning the healthcare site to a different COT.

18. The at least one computer-readable non-transitory storage medium of claim 17, wherein the processor-executable instructions, in response to further execution, further cause the computing system to cause a computing device to present a user interface (UI) comprising a UI element indicative of the recommendation.

19. The at least one computer-readable non-transitory storage medium of claim 18, wherein the user interface further comprises at least one of an identifier for the healthcare site, a chart conveying a first data view associated with the recommendation, or a table conveying a second data view associated with the recommendation.

20. The computing system of claim 1, wherein the API accesses the data indicative of the recommendation via a function call.

* * * * *